(12) United States Patent
Makino

(10) Patent No.: US 6,878,165 B2
(45) Date of Patent: Apr. 12, 2005

(54) NASOLACRIMAL DUCT TUBE USED FOR LACRIMAL DUCT REFORMATION OPERATION, AND NASOLACRIMAL DUCT TUBE INSTRUMENT

(75) Inventor: Hiroyuki Makino, Ikoma (JP)

(73) Assignees: Toray Industries, Inc., Tokyo (JP); Nakagawa, Akio, Kyoto-Fu (JP)

( * ) Notice: Subject to any disclaimer, the term of this patent is extended or adjusted under 35 U.S.C. 154(b) by 419 days.

(21) Appl. No.: 10/030,345

(22) PCT Filed: Mar. 13, 2001

(86) PCT No.: PCT/JP01/01986
§ 371 (c)(1),
(2), (4) Date: Nov. 7, 2001

(87) PCT Pub. No.: WO01/67995
PCT Pub. Date: Sep. 20, 2001

(65) Prior Publication Data
US 2002/0107579 A1 Aug. 8, 2002

(30) Foreign Application Priority Data
Mar. 14, 2000 (JP) ........................................ 2000-070248

(51) Int. Cl.$^7$ .............................. A61F 2/04; A61M 5/00
(52) U.S. Cl. ............................................. 623/10; 604/8
(58) Field of Search ............................... 623/10; 604/8; 606/107–108, 264

(56) References Cited
U.S. PATENT DOCUMENTS

| | | | |
|---|---|---|---|
| 4,658,816 A | * | 4/1987 | Ector, Jr. .......................... 606/2 |
| 5,345,948 A | * | 9/1994 | O'Donnell, Jr. ............. 128/898 |
| 5,437,625 A | * | 8/1995 | Kurihashi ......................... 604/8 |
| 5,792,100 A | * | 8/1998 | Shantha ........................ 604/509 |
| 6,117,116 A | * | 9/2000 | Walsh .......................... 604/264 |
| 6,383,192 B1 | * | 5/2002 | Kurihashi .................... 606/108 |
| 6,547,765 B1 | * | 4/2003 | Walsh et al. ................. 604/264 |
| 6,605,108 B2 | * | 8/2003 | Mendius et al. ............ 623/1.11 |

FOREIGN PATENT DOCUMENTS

| | | |
|---|---|---|
| JP | 4364842 | 12/1992 |
| JP | 5317351 | 12/1993 |

* cited by examiner

Primary Examiner—David H. Willse
Assistant Examiner—Suzette J. Gherbi
(74) Attorney, Agent, or Firm—Ladas & Parry LLP

(57) ABSTRACT

A nasolacrimal stent device illuminates a dark nasal cavity so that the interior of the nasal cavity can be directly observed to facilitate and ensure the correct insertion of a nasolacrimal stent into the nasal duct. Flexible, transparent probe tube segments (21) are connected to the opposite ends of a flexible detention tube segment (2) having a diameter that permits the flexible detention tube segment (2) to be inserted in a lacrimal passage, respectively. The respective extremities of distal end parts (21a, 21b) of the probe tube segments (21) are closed. The probe tube segments (21) are provided in their base end parts with openings (23), respectively. When inserting each probe tube segment (21) into the nasal cavity, an illuminating device, such as an optical fiber (30) is inserted through the opening (23) into the probe tube segment (21) to illuminate the interior of the nasal cavity through the transparent probe tube segment (21). The probe tube segment (21) can be surely caught with a hook and can be pulled out from the nasal cavity. An ultrasonic probe or an endoscope may be used instead of the illuminating device to find the position of the nasolacrimal stent in the nasal cavity.

18 Claims, 7 Drawing Sheets

NASOLACRIMAL DUCT TUBE USED FOR LACRIMAL DUCT REFORMATION OPERATION, AND NASOLACRIMAL DUCT TUBE INSTRUMENT

TECHNICAL FIELD

The present invention relates to a nasolacrimal stent to be employed in operations for the plastic surgery of a lacrimal punctum, a canaliculus, a lacrimal sac or a lacrimal passage of a nasolacrimal duct for the treatment of lacrymatory diseases.

BACKGROUND ART

Referring to FIG. 15 showing the nose and the eye E of a man, the interior of the eye E communicates with a superior canaliculus 2a and an inferior canaliculus 2b by means of small pores opening in a medial part of the eye E on the side of the nose, i.e., a superior lacrimal punctum 1a and an inferior lacrimal punctum 1b. The superior canaliculus 2a and the inferior canaliculus 2b communicate with a lacrimal sac 4 by means of a collective canaliculus 3. The lacrimal sac 4 connects with a nasolacrimal duct 5 extending downward and opening into an inferior nasal meatus 6. In FIG. 15, indicated at 7 is a middle nasal meatus and at 8 is a middle turbinate bone.

A lacrimal silicone tube is a nasolacrimal stent for the plastic surgery of the lacrimal passage including a lacrimal punctum, a canaliculus, a lacrimal sac and a nasolacrimal duct. The lacrimal silicone tube is applied often to lacrimal passage plastic surgery and canaliculus plastic surgery as a stent, and as an insert to the prevention of dacryostenosis as a complication of radiotherapy.

FIGS. 16 and 17 are views of assistance in explaining a method of using a silicone tube device provided with such a silicone tube. As shown in FIG. 16, the silicone tube device has a flexible silicone tube 9, and metal probes 10 having the shape of a rod and connected to the opposite ends of the silicone tube 9, respectively. Each probe 10 has a distal end formed in a bulge 11. As shown in FIG. 17, when using the silicone tube device, the probes 10 are inserted through the superior lacrimal punctum 1a and the inferior lacrimal punctum 1b, and the lacrimal sac 4 into the nasolacrimal duct 5. First the bulges 11 formed at the distal ends of the probes 10 are inserted through the superior lacrimal punctum 1a and the inferior lacrimal punctum 1b into the superior canaliculus 2a and the inferior canaliculus 2b, respectively. The probes 10 are inserted deeper into the nasal cavity and a special hook 12 is engaged with each bulge 11 to pull out the probe 10 from the nasal duct as shown in FIG. 17. Thus, the silicone tube 9 can be extended through the lacrimal puncta 1a and 1b and the inferior nasal meatus by the guiding action of the probes 10. After such silicon tube inserting work has been completed, the probes 10 are disconnected from the silicone tube 9 when necessary, and opposite end parts of the silicone tube 9 are tied in a knot 13 so that the silicone tube 9 may not come off as shown in FIG. 18. Thus, the silicone tube 9 is left in the body as a stent to keep the lacrimal passage unobstructed.

Particularly, the lacrimal sac 4 and the nasolacrimal duct are dark. Therefore the silicon tube device must be operated by feel in the nasal duct when inserting the silicon tube device into the lacrimal passage, and hence it often occurs that the silicon tube device deviates from a correct passage, a false passage is formed in tissues, and nasal mucous membranes are damaged causing massive hemorrhage. Thus the work for the insertion of the silicon tube device in the lacrimal passage is very difficult. To avoid such troubles and to overcome such difficulties, there have been proposed a silicone tube device inserting method that uses an endoscope for the observation of the lacrimal passage, and a silicone tube device inserting method that uses a surgical lamp for illumination. However, the former method requires difficult work to use fingers for surgical operations, observing pictures taken by an endoscope and displayed on a monitor. The use of a surgical lamp is not perfectly effective because it is difficult to illuminate the interior of the nasal duct directly with the surgical lamp.

The present invention has been made to solve those problems and it is therefore an object of the present invention to provide a nasolacrimal stent which can be surely and readily pulled through the nasal duct and pulled out of the nasal duct for intubation without damaging nasal mucous membranes and without causing massive hemorrhage, and to provide a nasolacrimal stent device.

DISCLOSURE OF THE INVENTION

According to the present invention, a nasolacrimal stent for lacrimal passage plastic surgery includes a flexible tube having a diameter that permits the flexible tube to be inserted and detained in a lacrimal passage, and provided with at least one opening formed in a part thereof at a predetermined distance from one of the opposite ends thereof, wherein distal end parts of the flexible tube are tapered and have rounded tips, respectively. Desirably, the opening of the flexible tube is formed in a bend formed by bending a part of the flexible tube at an angle to the other part of the same.

The flexible tube may include a flexible detention tube segment, and flexible probe segments connected to the opposite ends of the detention tube segment, respectively, and the opening may be formed in the probe tube segment.

According to the present invention, a nasolacrimal stent device for lacrimal passage plastic surgery includes a flexible tube capable of being inserted and detained in a lacrimal passage and provided with at least an opening formed in a part thereof at a predetermined distance from one of the opposite ends thereof, and an illuminating device capable of being inserted in and extracted from the flexible tube through the opening formed in the flexible tube. The illuminating device may be an optical fiber or a light-emitting device.

According to the present invention, a nasolacrimal stent device for lacrimal passage plastic surgery includes a flexible tube capable of being inserted and detained in a lacrimal passage, provided with at least one opening in a part thereof at a predetermined distance from one of the opposite ends thereof, and a tube-position finding means capable of being inserted in and extracted from the flexible tube through the opening formed in the flexible tube. The tube-position finding means may be an ultrasonic probe or an endoscope.

BEST MODE FOR CARRYING OUT THE INVENTION

A preferred embodiment of the present invention will be described hereinafter.

Figure 1:
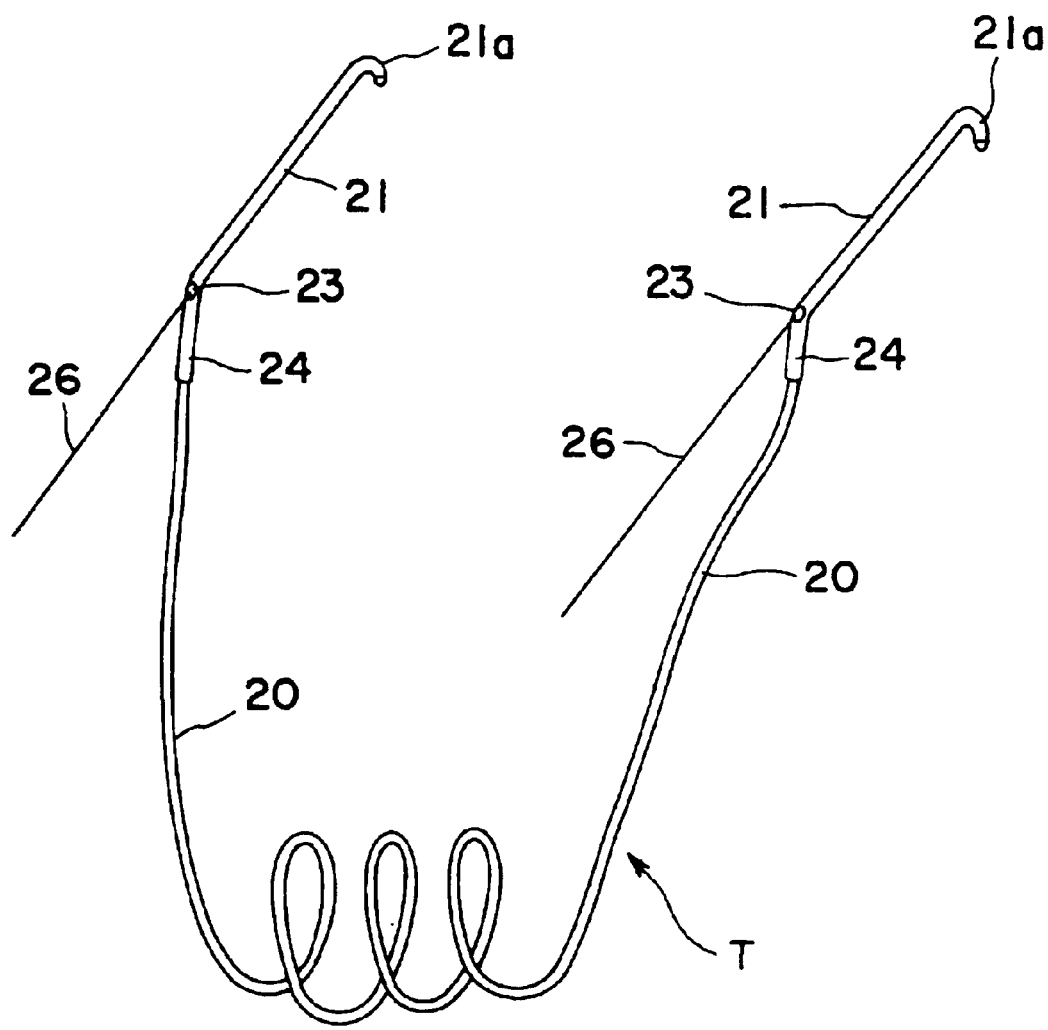
FIG. 1 is a perspective view of a nasolacrimal stent device in a preferred embodiment according to the present invention for lacrimal passage plastic surgery

Referring to FIG. 1, a nasolacrimal stent and a nasolacrimal stent device in a preferred embodiment according to the present invention for lacrimal passage plastic surgery includes a tube T having a detention tube segment 20 and flexible, light-transmitting (transparent or translucent) first and second probe tube segments 21 connected to the opposite ends of the flexible detention tube segment 20, respectively. The flexible detention tube segment 20, similarly to a conventional one, may be formed of silicone. The probe tube segments 21 may be formed of, for example, a polyolefin resin, a polyamide resin, a polyurethane resin or a mixture of some of those resins. Tubes of those resins including polyolefin resins are harder and more excellent in shape retention than silicone tubes, and can be readily inserted in the lacrimal passage. Preferably, the inside diameter of the detention tube segment 20 is, for example, in the range of about 0.05 to about 3.5 mm, more preferably, in the range of about 0.5 to abut 0.6 mm. Preferably, the outside diameter of the probe tube segments 21 is, for example, in the range of about 0.1 to about 4.0 mm, more preferably, about 1.1 mm. The detention tube segment 20 and the probe tube segments 21 of the tube T may be formed of one and the same material in one piece.

Figure 2:
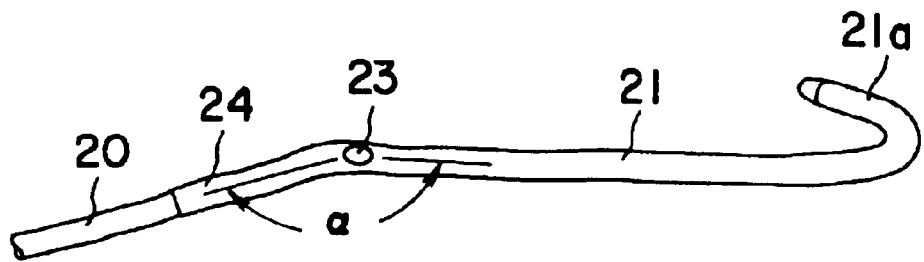
FIG. 2 is an enlarged view of a probe tube segment and a detention tube segment of the nasolacrimal stent device shown in FIG. 1.

Base end parts 24 of the probe tube segments 21 are joined to the opposite ends of the detection tube segment 20. A distal end part 21a of each probe tube segment 21 is tapered toward its closed, spherical tip to facilitate an operation for inserting the distal end part 21a in a lacrimal punctum or the like. As best shown in FIG. 2, the distal end part 21a is bent in the shape of a hook. An opening 23 is formed in a part of the probe tube segment 21 near the end of the base end part 24. A fine metal bougie, and a very thin illuminating device, such as an optical fiber, or a tube position finding means are inserted through the opening 23 in the probe tube segment 21. An edge part of the opening 23 must be strengthened so that the same may not break. The closed distal end part 21a of the probe tube segment 21 has a hardness high enough to withstand a piercing force that may be exerted thereon by the tip of the fine metal bougie. Although it is desirable that the tip of the distal end part 21a is closed, the same may be opened to an extent that will not constitute an obstacle to the function of the probe tube segment 21. A part of the probe tube segment 21 including the opening 23 is bent such that the axis of the base end part 24 is inclined at an angle α to that of the probe tube segment 21. The opening 23 is formed in the outer corner of the bent part. The angle α is on the order of 5°. In the tube T shown in FIG. 1, the openings 23 are formed in both the bent parts at a predetermined distance from the corresponding tips of the opposite distal end parts 21a, one of the openings 23 may be omitted.

Figure 3:
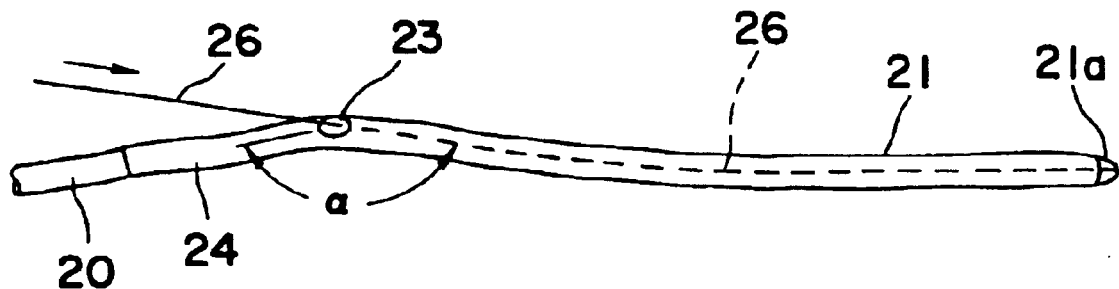
FIG. 3 is a view, similar to FIG. 2, of assistance in explaining an operation for inserting a fine metal bougie through an opening formed in the probe tube segment shown in FIG. 2 in the same probe tube segment.
Figure 5:
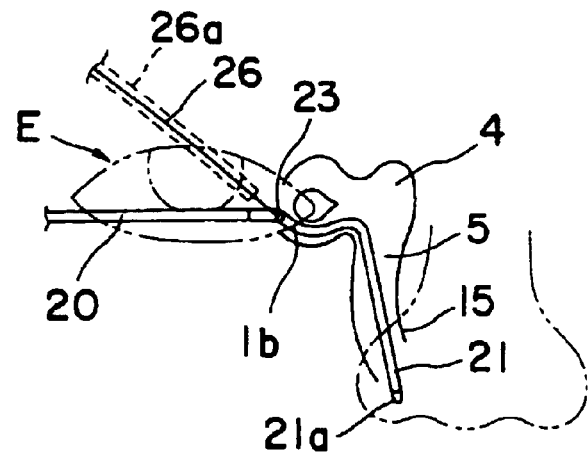
FIG. 5 is a view of assistance in explaining the first step of lacrimal passage plastic surgery using the nasolacrimal stent device of the present invention.

A fine metal bougie 26 and a very thin optical fiber 30 to be included in a nasolacrimal stent device according to the present invention will be described. Referring to FIG. 3, the bougie 26 is a flexible, shape-retaining, very fine metal wire. The bougie 26 is formed in a diameter that permits the insertion of the bougie 26 through the opening 23 into the probe tube segment 21. As shown in FIG. 5, a grip 26a is put on a base end part of the bougie 26. The bougie 26 is gripped by the grip 26a when operating the bougie 26.

Figure 4:
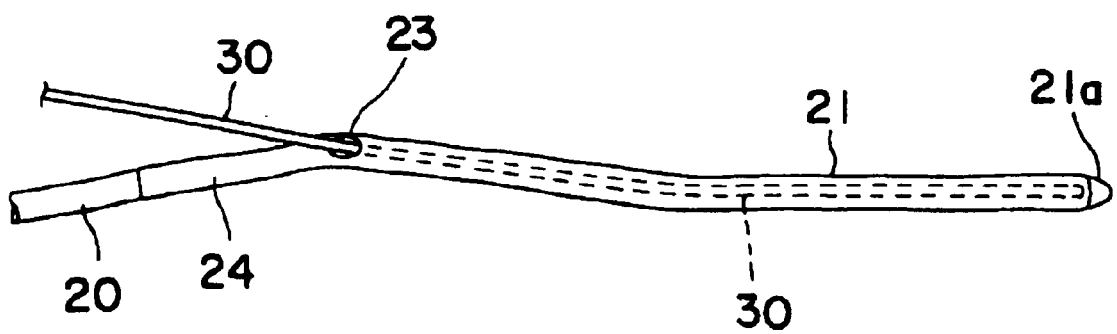
FIG. 4 is a view, similar to FIG. 2, of assistance in explaining an operation for inserting an optical fiber, i.e., an illuminating device, through the opening formed in the probe tube segment in the same probe tube segment.

Referring to FIG. 4, the optical fiber 30, similarly to the bougie 26, is flexible and very thin and is formed in a diameter that permits the insertion of the optical fiber 30 through the opening 23 into the probe tube segment 21. The optical fiber 30 transmits light emitted by a light source 31 (FIG. 8) and fallen on one end of the optical fiber 30, repeatedly reflecting the same therein. The illuminating device may be any suitable linear illuminating device other than the optical fiber. The optical fiber, which transmits light emitted by a light source, may be substituted by a self-luminous linear device of a self-luminous material, such as a luminous pigment. The self-luminous linear device of a self-luminous material must be flexible and very thin and has a diameter that permits the line to be inserted through the opening 23 into the probe tube segment 21.

A method of using the nasolacrimal tube device thus constructed will be described.

First, a fine metal bougie 26 is inserted through the opening 23 in the first probe tube segment 21 as shown in FIG. 3. The fine metal bougie 26 can be readily inserted through the opening 23 into the first probe tube segment 21 because the opening 23 is formed in the outer corner of the bent part of the first probe tube segment 21. The straight bougie 26 can be inserted in the first probe tube segment 21 so deep that the straight bougie 26 reaches the extremity of the interior of the first probe tube segment 21 as indicated by a dotted line in FIG. 3. Since the bougie 26 is straight, the hooked distal end part 21a of the first probe tube segment 21 is straightened when the straight bougie 26 is inserted deep into the first probe tube segment 21 as indicated by a dotted line in FIG. 3.

The distal end part 21a of the thus straightened first probe tube segment 21 as shown in FIG. 3 is inserted through the inferior lacrimal punctum 1b into the lacrimal passage. The distal end part 21a is advanced through the canaliculus 2b, the collective canaliculus 3 and the lacrimal sac 4 to a position shown in FIG. 5. In this state, the distal end part 21a of the first probe tube segment 21 lies on the nasal bottom wall 15. Completion of the operation for placing the first probe tube segment 21 at a predetermined position can be confirmed by the arrival of the opening 23 at a position close to the inferior lacrimal punctum 1b.

Figure 6:
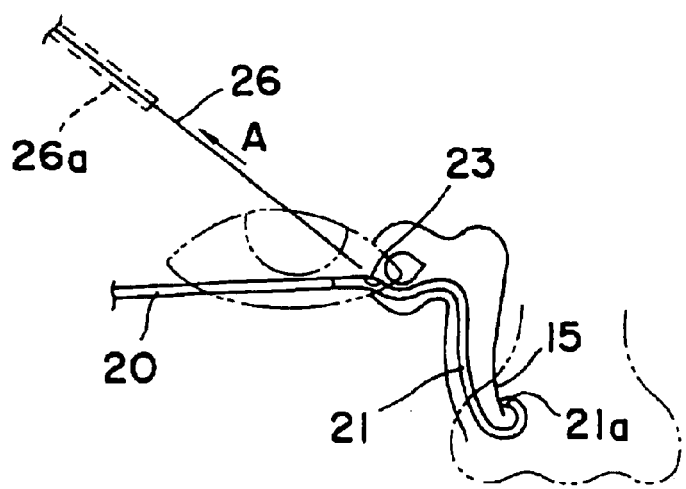
FIG. 6 is a view of assistance in explaining the second step of lacrimal passage plastic surgery using the nasolacrimal stent device of the present invention.

After the confirmation of placement of the first probe tube segment 21 in a state shown in FIG. 5, the fine metal bougie 26 is gripped by the grip 26a and is pulled in the direction of the arrow A to extract the same from the first probe tube segment 21. Consequently, the distal end part 21a is permitted to return to its original hooked shape as shown in FIG. 6. The hooked distal end part 21a touches the nasal bottom wall 15 to hold the first probe tube segment 21 securely in place.

Figure 7:
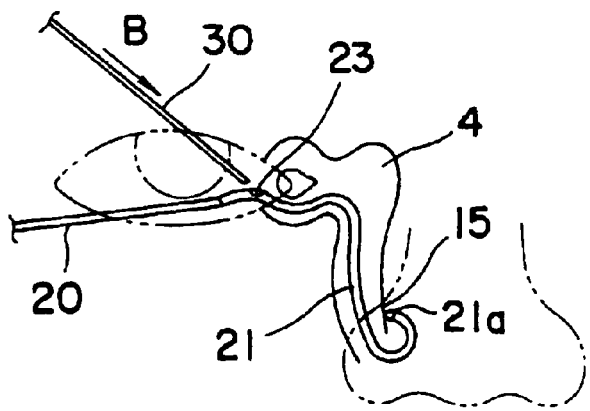
FIG. 7 is a view of assistance in explaining the third step of lacrimal passage plastic surgery.

Subsequently, the optical fiber 30, i.e., a luminous device featuring the present invention, is pushed in the direction of the arrow B in FIG. 7 to insert the same through the opening 23 into the first probe tube segment 21. The bend around the opening 23 facilitates an operation for inserting the optical fiber 30 into the first probe tube segment 21. FIG. 4 shows the optical fiber 30 inserted in the first probe tube segment 21. The distal end part 21a retains its hooked shape and remains in contact with the nasal bottom wall to retain the first probe tube segment 21 in place after the optical fiber 30 has been properly inserted in the first probe tube segment 21 because the optical fiber 30 has a low shape retaining property.

Figure 8:
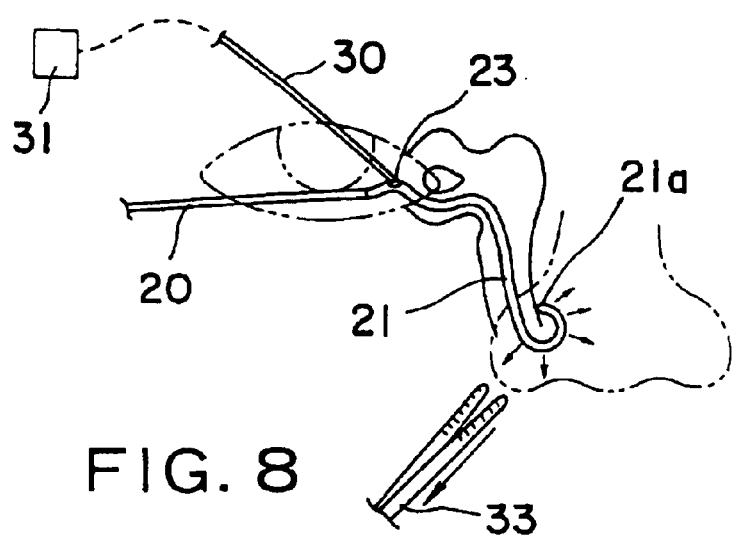
FIG. 8 is a view of assistance in explaining the fourth step of lacrimal passage plastic surgery.
Figure 9:
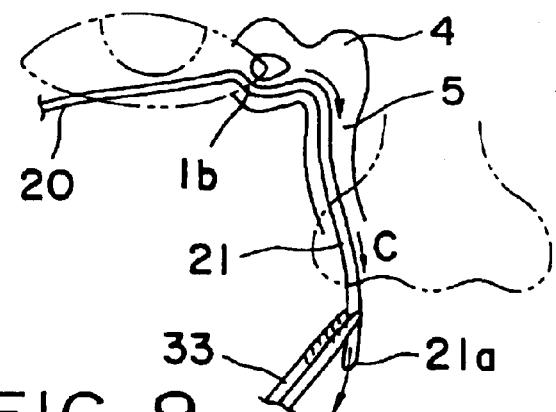
FIG. 9 is a view of assistance in explaining the fifth step of lacrimal passage plastic surgery.

After the optical fiber 30 has been thus inserted into the first probe tube segment 21, light emitted by the light source 31 is introduced into the optical fiber 30 as shown in FIG. 8. Consequently, the optical fiber inserted in the first probe tube segment 21 becomes luminous, whereby the dark nasal cavity is illuminated because the first probe tube segment 21 is a light-transmitting (transparent or translucent) tube. Thus, the operator is able to observe the interior of the nasal cavity directly. The operator expands the nostril with a nasoscope and inserts nasal forceps or a hook 33 in the nostril. The operator is able to catch the distal end part 21a of the luminous first probe tube segment 21 firmly with the nasal forceps or the hook 33 and is able to pull the first probe tube segment 21 in the direction of the arrow C shown in FIG. 9 to pull out the first probe tube segment 21 from the nasal cavity.

Figure 10:
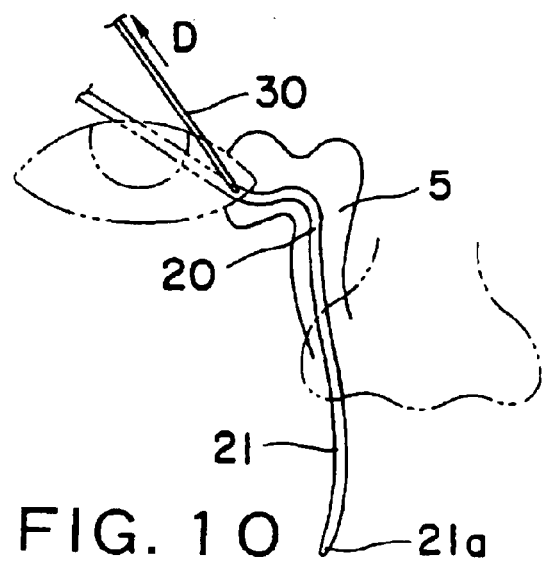
FIG. 10 is a view of assistance in explaining the sixth step of lacrimal passage plastic surgery.

Consequently, the detention tube segment 20 continuous with the first probe tube segment 21 is pulled through the inferior lacrimal punctum 1b, the inferior canaliculus 2b and the lacrimal sac 4 into the nasolacrimal duct 5 as shown in FIG. 10. In this state, the opening 23 lies in the nasal cavity. Then, the optical fiber 30 is pulled in the direction of the arrow D shown in FIG. 10 to extract the same from the first probe tube segment 21. Then, the first probe tube segment 21 becomes unluminous.

Figure 11:
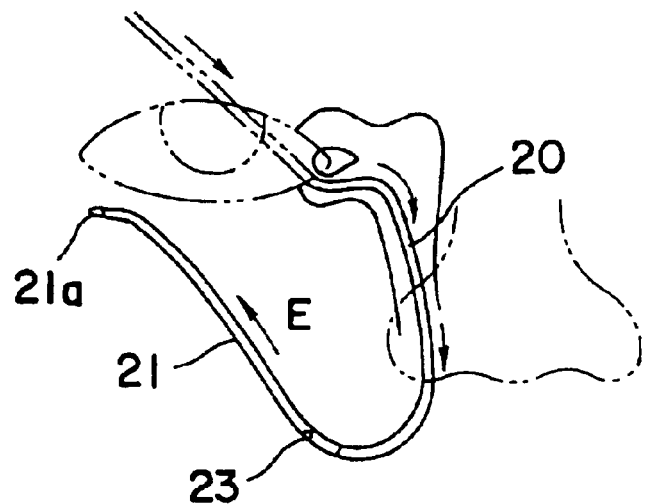
FIG. 11 is a view of assistance in explaining the seventh step of lacrimal passage plastic surgery.

Subsequently, the first probe tube segment 21 is pulled further in the direction of the arrow E as shown in FIG. 11 to pull out a part of the detention tube segment 20 from the nostril. Thus, the operation for inserting the detention tube segment 20 through the inferior lacrimal punctum 1b in the nasolacrimal duct 5 is completed.

Subsequently, the second probe tube segment 21 and the other part of the detention tube segment 20 are inserted through the superior lacrimal punctum 1a. A procedure for inserting the second probe tube segment 21 and the other part of the detention tube segment 20 through the superior lacrimal punctum 1a is basically the same as the foregoing procedure for inserting the first probe tube segment 21 and the detention tube segment 20 through the inferior lacrimal punctum 1b. The procedure will be described with reference to FIGS. 12 to 14.

Figure 12:
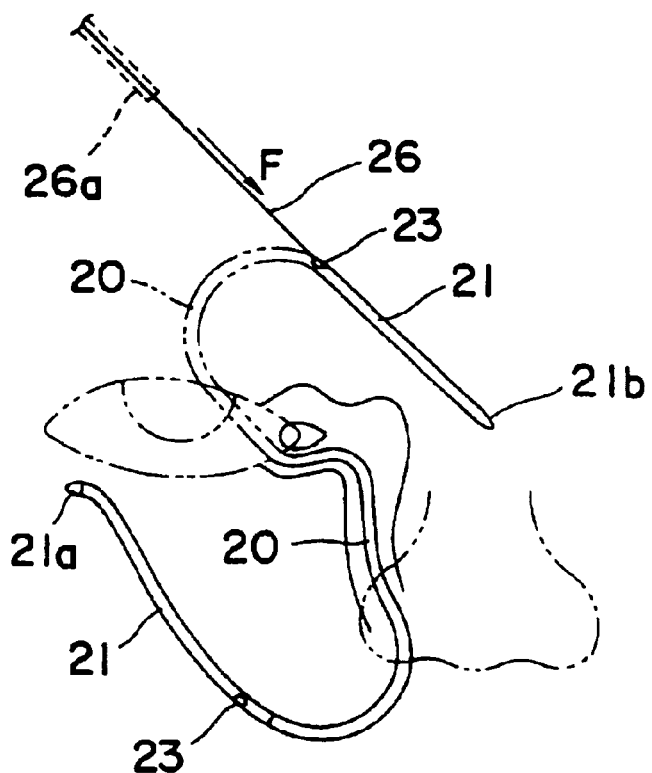
FIG. 12 is a view of assistance in explaining the eighth step of lacrimal passage plastic surgery.
Figure 13:
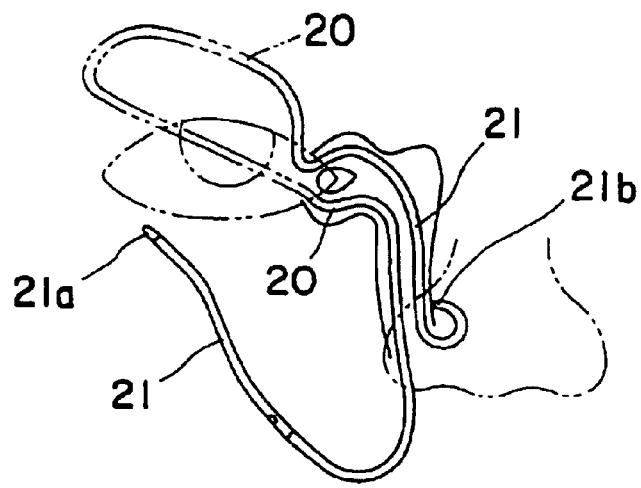
FIG. 13 is a view of assistance in explaining the ninth step of lacrimal passage plastic surgery.

Referring to FIG. 12, a fine metal bougie 26 is pushed in the direction of the arrow F to insert the bougie 26 through the opening 23 formed in the second probe tube segment 21 into the second probe tube segment 21. The distal end part of the second probe tube segment 21 is indicated at 21b. The second probe tube segment 21 is inserted into the nasolacrimal duct 5 by the leading action of the bougie 26 so deep that the distal end part 21b touches the nasal bottom wall 15. Then, the bougie 26 is removed. Consequently, the distal end part 21b is permitted to return to its original hooked shape.

The hooked distal end part 21b touches the nasal bottom wall 15 to hold the second probe tube segment 21 securely in place.

Figure 14:
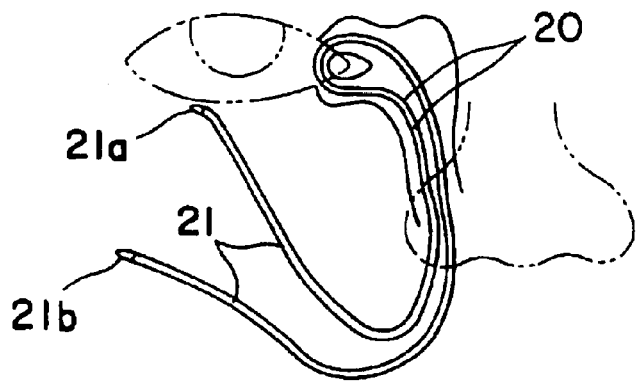
FIG. 14 is a view of assistance in explaining the tenth step of lacrimal passage plastic surgery.
Figure 15:
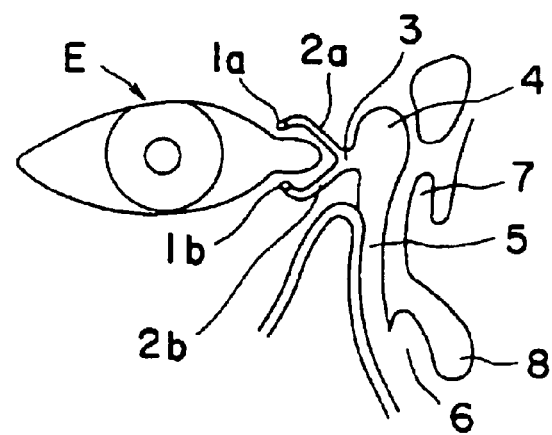
FIG. 15 is a view of assistance in the medical explanation of a lacrimal passage and the associated parts.
Figure 16:
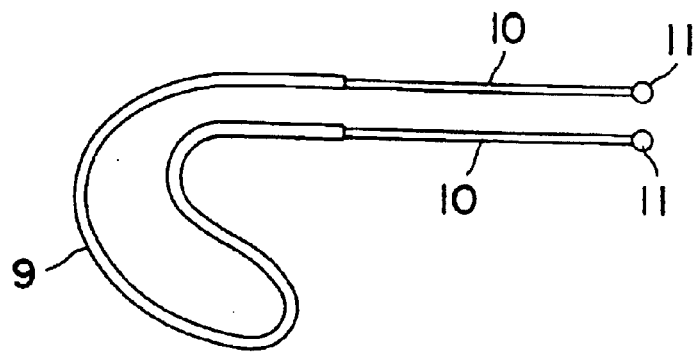
FIG. 16 is a perspective view of a conventional nasolacrimal stent.
Figure 17:
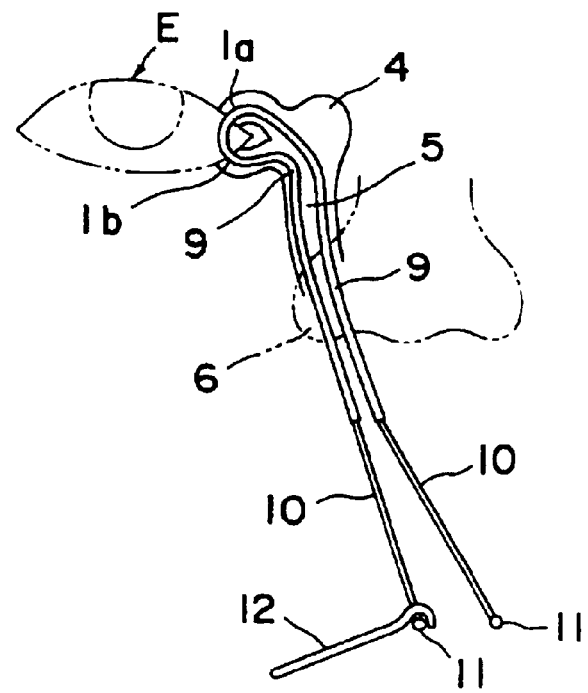
FIG. 17 is a view of the conventional nasolacrimal stent in use.
Figure 18:
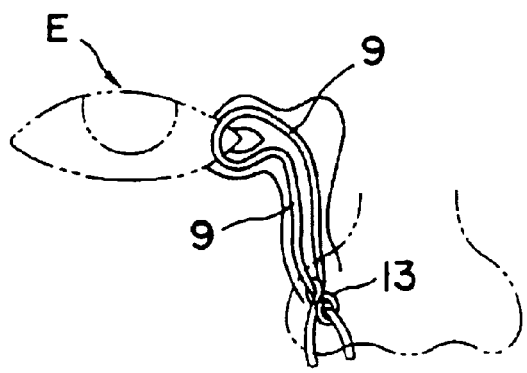
FIG. 18 is a view the conventional nasolacrimal stent detained in a nasolacrimal duct.

After the bougie 26 has been extracted from the second probe tube segment 21, the optical fiber 30 is inserted into the second probe tube segment 21 by the same optical fiber inserting operation, not shown, and light is introduced into the optical fiber 30. Consequently, the second probe tube segment 21 installed in the nasal cavity becomes luminous, whereby the dark nasal cavity is illuminated. Thus, the operator is able to catch the distal end part 21b of the luminous second probe tube segment 21 firmly with the hook and is able to pull the second probe tube segment 21 to pull out the second probe tube segment 21 from the nasal cavity. Then, the same procedure as that mentioned above is carried out to extract the optical fiber 30 from the second probe tube segment 21 and to pull out the second probe tube segment 21 from the nasal cavity as shown in FIG. 14. In a state shown in FIG. 14, both the end parts of the detention tube segment 20 are inserted through the superior lacrimal punctum 1a and the inferior lacrimal punctum 1b, respectively, into the lacrimal passage and are pulled out of the nasal cavity. The probe tube segments 21 are separated from the detention tube segment 20, opposite end parts of the detention tube segment 20 are tied in a knot 13 as shown in FIG. 19 so that the detention tube segment 20 is unable to move. Thus, a series of steps of a procedure for installing the nasolacrimal stent in the nasal cavity is completed.

The foregoing procedure is applied also to installing the nasolacrimal stent using a self-luminous linear device instead of the optical fiber 30.

Although the foregoing embodiment employs an illuminating device, such as the optical fiber 30 or the self-luminous linear device, a tube position finding means, such as an ultrasonic probe or an endoscope, capable of finding the position of the probe tube segment 21 in the lacrimal passage or the nasal cavity may be used instead of the illuminating device. When an ultrasonic probe is employed, the ultrasonic probe must be formed in the shape of a thin wire because the ultrasonic probe must be inserted into and pulled out of the probe tube segment 21 through the opening 23, which holds true for an endoscope. The ultrasonic probe emits ultrasonic waves and determines whether or not the probe tube segment has deviated from a correct passage on the basis of the condition of the reflected ultrasonic waves. The operator is able to know a passage through which the probe tube segment is passed from the condition of the reflected ultrasonic waves. When the ultrasonic probe is employed, the probe tube segments do not need necessarily to be transparent. When the endoscope is employed, the probe tube segments must be transparent because matters outside the probe tube segments must be observed through the probe tube segments.

As apparent from the foregoing description, according to the present invention, an illuminating device and a tube position finding means can be inserted in and extracted from a tube through an opening formed in the tube. Therefore, when inserting the nasolacrimal stent into the nasal cavity, the nasolacrimal stent becomes luminous when an illuminating device is sued, and operations in the dark nasal cavity can be easily and correctly carried out because the nasal duct is illuminated and can be directly observed. When the tube position finding means is employed, the passage through which the nasolacrimal stent is passed can be found by the tube position finding means. Therefore, troubles, such as the formation of a false passage in tissues due to the deviation of the probe tube segment from a correct passage and the resultant massive hemorrhage, can be avoided.

Since the part provided with the opening of the probe tube segment of the nasolacrimal stent is bent at a predetermined angle, the illuminating device and the tube position finding means can be readily inserted in and extracted from the probe tube segment.

The bougie inserted in the probe tube segment so as to be removable ensures the proper insertion of the probe tube segment in the lacrimal passage.

The hooked distal end part of the probe tube segment holds to the nasal bottom wall and is capable of surely preventing the probe tube segment from coming off the nasal cavity during the operation.

Moreover, the probe tube segment exercises a satisfactory probing effect when the same is formed of a material having a satisfactory shape-retaining property, such as a polyolefin resin, a polyamide resin, a polyurethane resin or a mixture of some of those resins.

What is claimed is:

1. A nasolacrimal stent for lacrimal passage plastic surgery comprising a flexible detention tube having a diameter capable of permitting the flexible detention tube to be inserted and detained in a lacrimal passage, and provided with at least one opening formed in a part thereof at a predetermined distance from one of opposite ends thereof;

wherein distal end parts of the flexible tube are tapered and have rounded tips, respectively, and wherein the flexible tube includes a flexible detention tube segment, and flexible probe segments connected to opposite ends of the detention tube segment, respectively, so as to be continuous with the detention tube segment.

2. The nasolacrimal stent for lacrimal passage plastic surgery according to claim 1, wherein the opening of the flexible tube is formed in an outer corner of a bend formed by bending a part of the flexible tube at an angle to the other part of the same.

3. The nasolacrimal stent for lacrimal passage plastic surgery according to claim 1, wherein the probe tube segments are formed of a transparent material.

4. The nasolacrimal stent for lacrimal passage plastic surgery according to claim 1, wherein the distal end parts of the probe tube segments are bent elastically in the shape of a hook.

5. The nasolacrimal stent for lacrimal passage plastic surgery according to claim 1, wherein the probe tube segments are formed of a polyolefin resin, a polyamide resin, a polyurethane resin of a mixture of some of those resins.

6. A nasolacrimal stent device for lacrimal passage plastic surgery comprising:

a flexible tube capable of being inserted and detained in a lacrimal passage and provided with at least an opening formed in a part thereof at a predetermined distance from one of opposite ends thereof; and an illuminating device capable of being inserted in and extracted from the flexible tube through the opening formed in the flexible tube, wherein the flexible tube includes a flexible detention tube segment and flexible, transparent probe tube segments connected to opposite ends of the flexible detention tube segment so as to be continuous with the flexible detention tube segment.

7. The nasolacrimal stent device for lacrimal passage plastic surgery according to claim 6, wherein the opening of the flexible tube is formed in an outer corner of a bend formed by bending a part of the flexible tube at an angle to the other part of the same.

8. The nasolacrimal stent device for lacrimal passage plastic surgery according to claim 6, wherein the illuminating device is an optical fiber, and a light source is connected to the optical fiber.

9. The nasolacrimal stent device for lacrimal passage plastic surgery according to claim 6, wherein the illuminating device is a self-luminous device.

10. The nasolacrimal stent device for lacrimal passage plastic surgery according to claim 6, wherein the flexible tube comprises distal end parts, and the distal end parts of the flexible tube are bent elastically in the shape of a hook.

11. The nasolacrimal stent device for lacrimal passage plastic surgery according to claim 6 further comprising a bougie formed from a wire and capable of being inserted in and extracted from the flexible tube through the opening.

12. A nasolacrimal stent device for lacrimal passage plastic surgery comprising:

a flexible tube having a diameter that permits the flexible tube to be inserted and detained in a lacrimal passage, and provided with at least one opening formed in a part thereof at a predetermined distance from one of opposite ends thereof; and a tube position finding means for and capable of ascertaining the position of the flexible tube in a lacrimal passage or nasal cavity, said tube position finding means being capable of being inserted in and of being extracted from the flexible tube through the opening formed in the flexible tube.

13. The nasolacrimal stent device for lacrimal passage plastic surgery according to claim 12, wherein the flexible tube includes a flexible detention tube segment, and flexible probe tube segments connected to opposite ends of the flexible detention tube segment, respectively, and the opening is formed in the flexible probe tube segment.

14. The nasolacrimal stent device for lacrimal passage plastic surgery according to claim 12, wherein a part of the flexible tube provided with the opening is bent at an angle in a bend, and the opening is formed in an outer corner of the bend.

15. The nasolacrimal stent device for lacrimal passage plastic surgery according to claim 12, wherein the tube position finding means is an ultrasonic probe.

16. The nasolacrimal stent device for lacrimal passage plastic surgery according to claim 12, wherein the flexible tube compresses probe tube segments, wherein the probe tube segments are formed of a transparent material, and the tube position finding means is an endoscope.

17. The nasolacrimal stent device for lacrimal passage plastic surgery according to claim 12, wherein distal end parts of the flexible tube assume a hooked shape in a free state.

18. The nasolacrimal stent device for lacrimal passage plastic surgery according to claim 12 further comprising a bougie formed from a wire and capable of being inserted in and extracted from the flexible tube through the opening.

* * * * *